United States Patent [19]

Ryder et al.

[11] Patent Number: 4,770,632

[45] Date of Patent: Sep. 13, 1988

[54] DELIVERY SYSTEM FOR DENTAL TREATMENT SOLUTION

[75] Inventors: Francis E. Ryder; Stephen P. Lisak, both of Arab, Ala.

[73] Assignee: National Patent Development Corporation, New York, N.Y.

[21] Appl. No.: 814,565

[22] Filed: Dec. 30, 1985

[51] Int. Cl.⁴ .............................................. A61C 1/02
[52] U.S. Cl. ....................................... 433/28; 433/80; 433/98; 433/101
[58] Field of Search ..................... 433/28, 80, 81, 82, 433/86, 88, 98, 101; 128/66

[56] References Cited

U.S. PATENT DOCUMENTS

| | | | |
|---|---|---|---|
| 3,213,537 | 10/1965 | Balamuth et al. | 433/86 |
| 3,863,628 | 2/1975 | Vit | 433/88 |
| 3,886,660 | 6/1975 | Thornton et al. | 433/98 |
| 4,078,558 | 3/1978 | Woog et al. | 128/66 |
| 4,137,911 | 2/1979 | Jousson | 128/66 |
| 4,148,309 | 4/1979 | Reibel | 128/66 |
| 4,247,288 | 1/1981 | Yoshii et al. | 433/81 |
| 4,607,627 | 8/1986 | Leber et al. | 128/66 |

Primary Examiner—John J. Wilson
Attorney, Agent, or Firm—Irene J. Frangos; Vincent P. Pirri

[57] ABSTRACT

The present invention relates to an improved delivery system for a dental treatment solution. More particularly, the apparatus disclosed includes a housing defining a well, a reservoir container for the dental treatment solution, and a pump for delivery of the solution to a hand piece. The pump includes an electrically energizable prime mover such as a motor or solenoid, a heater, and a control for the overall system. The control for the system provides a timing arrangement which is actuated upon placement of the reservoir container within the housing well, and which disables the system upon completion of the timing cycle. This feature, coupled with the employment of a visual signal, provides a dental professional with an indication of the strength or useful life of the dental treatment solution. Also disclosed are novel constructions for the pump and the heater, along with a novel design for the reservoir container.

45 Claims, 8 Drawing Sheets

DELIVERY SYSTEM FOR DENTAL TREATMENT SOLUTION

BACKGROUND OF THE INVENTION

The present invention relates to dental treatment with a caries removal solution, and more particularly to an improved delivery system for a dental treatment solution.

Use of a chemical solution for the removal of dental caries is well-known in the art, as are several types of delivery systems. In this regard, attention is directed to U.S. Pat. Nos. 3,776,825; 3,863,628; 3,886,266; 3,932,605; 3,943,628; 3,991,107; 4,012,842 and 4,060,600. The above-noted patents disclose in detail various formulations of the caries removal solution, certain methods of application of this solution to a decayed tooth, as well as one or more types of delivery systems for such a solution. The present invention, as will be discussed in greater detail hereinafter, relates to a delivery system where improved components are employed in the production of the pulsating jet of solution for delivery to the patient, the storage of the dental treatment solution, and the delivery of the solution to the pump means and from said pump means to the hand piece for application to a patient.

The caries removal dental treatment solutions are formed upon the mixing of two prepared solutions. First a starting halide such as sodium chloride, sodium bromide or the like as is more fully described in the above-noted patents, is provided. A second solution comprising an amino hydrogen compound is then provided and is mixed with the first solution to provide the N-halomine solution which when applied properly will effect removal of a dental caries. It should be noted, however, that the final solution is relatively unstable and once the various starting solutions have been mixed together the usable or pot life of the solution is about one hour.

The overall system or apparatus of the present invention includes basically a housing defining a well, a reservoir container for the dental treatment solution disposable in said well, pumping means for delivery of the solution to a hand piece, which pumping means includes an electrically energizable prime mover such as a motor or solenoid, heating means, and control means for the overall system. The control means for the system is significant in that there is provided a timing arrangement that is actuated upon placement of the reservoir container within the housing well upon completion of the timing cycle the control means will disable the motor or solenoid drive for the pump arrangement. This feature, coupled with the employment of a visual signal provides the dentist with an indication that the strength or useful life of the dental treatment solution has expired and that it is time to prepare a fresh solution.

As will be discussed in greater detail hereinafter, the present invention also provides numerous features which help to insure the stability of the dental treatment solution during use, as well as reliable delivery thereof to the patient. For example, the reservoir container is designed such that once positioned in the housing well, the lid cannot be opened for the addition of fresh solution, until such time as the entire reservoir container is removed. Further, the overall design of the housing and system is such that the electrical components are shielded from any spillage of the solution upon positioning of the reservoir container, or leakage of the solution from the internal tubings. The pumping means employed is of a novel design which facilitates ease of fabrication and assembly, and also provides a reliable performing pumping device, wherein the diaphragm stroke can be easily and accurately adjusted.

Further, there is provided a novel design for a reservoir container wherein the container includes an improved lid construction, as well as a transparent extension which will project through an opening in the housing to provide a visual indication of the level of dental treatment solution remaining in the reservoir. The housing is also designed so that this extension can be utilized as a finger grip to permit removal and insertion of the housing. Finally, there is also disclosed what is believed to be a novel arrangement for a heater that is employed to heat the dental treatment solution to approximately body temperature prior to delivery to the patient. This feature is primarily for the comfort of the patient, heating having little or no effect upon the caries removal solution.

BRIEF DESCRIPTION OF THE DRAWINGS

The various features of the present invention which are believed to be novel are set forth with particularity in the appended claims. The organization and manner of operation of the U invention, together with further objects and advantages thereof will best be understood by reference to the following detailed description taken in conjunction with the accompanying drawings in which like reference numerals identify similar elements, and wherein:

DETAILED DESCRIPTION OF THE ILLUSTRATED EMBODIMENT

Figure 1:
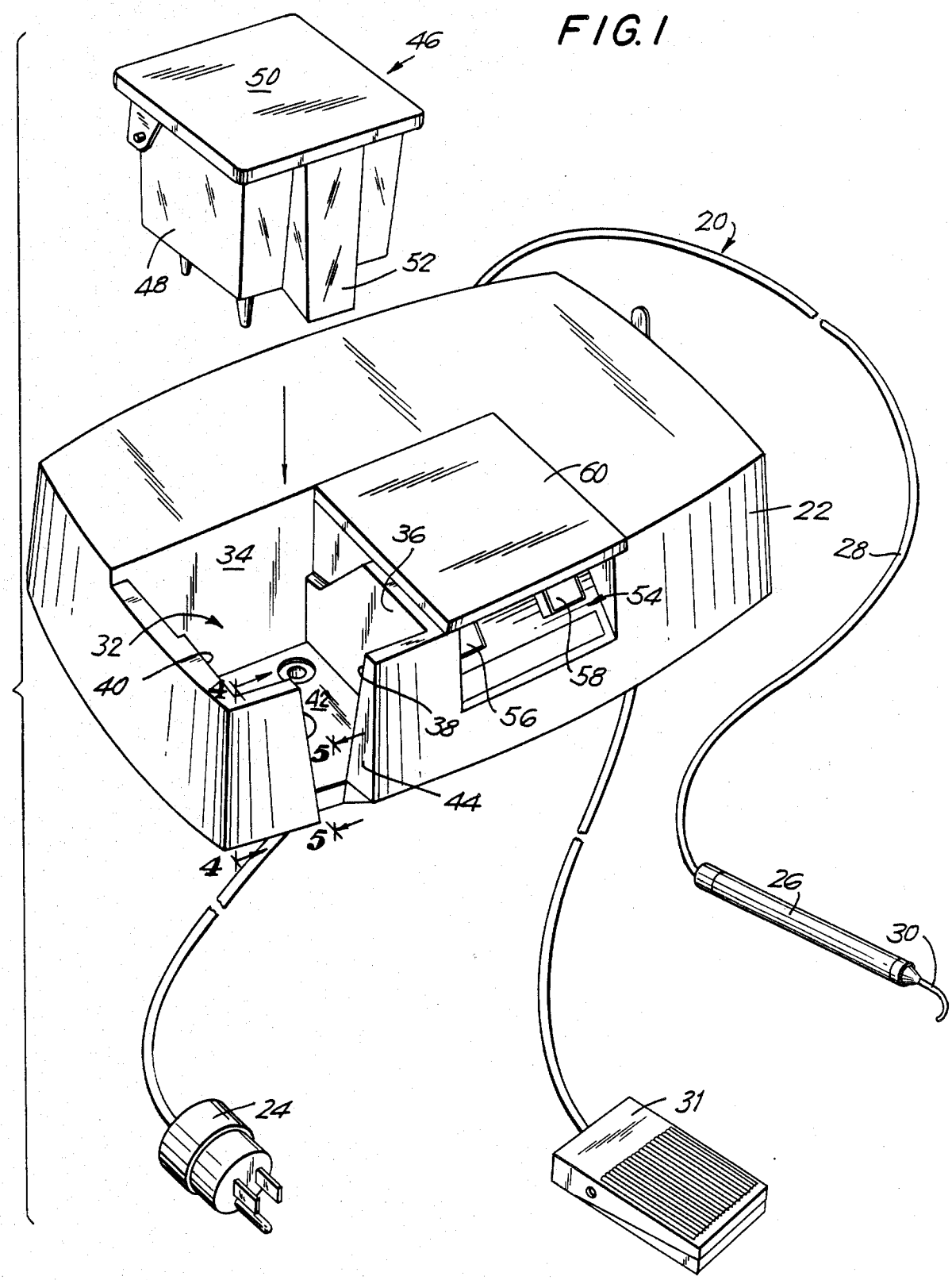
FIG. 1 is a perspective view of a delivery system in accordance with the present invention, with the reservoir container shown exploded from the overall apparatus housing.
Figure 2:
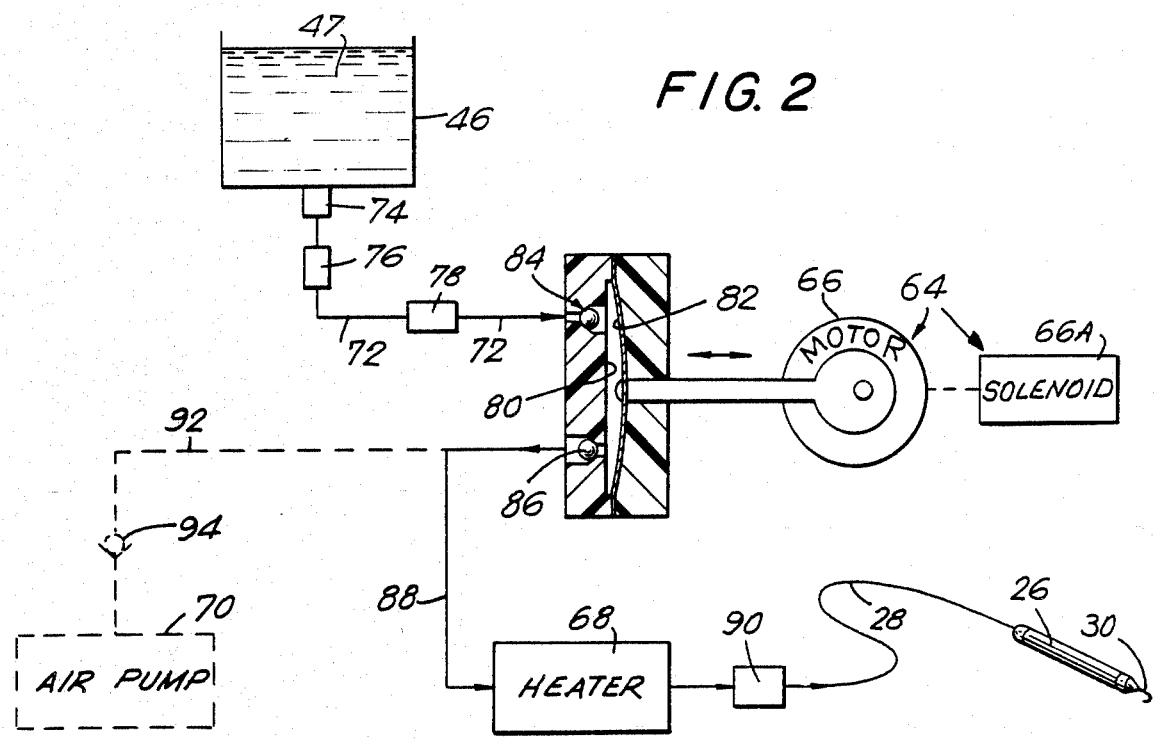
FIG. 2 is a mechanical schematic of the system of the present invention.
Figure 3:
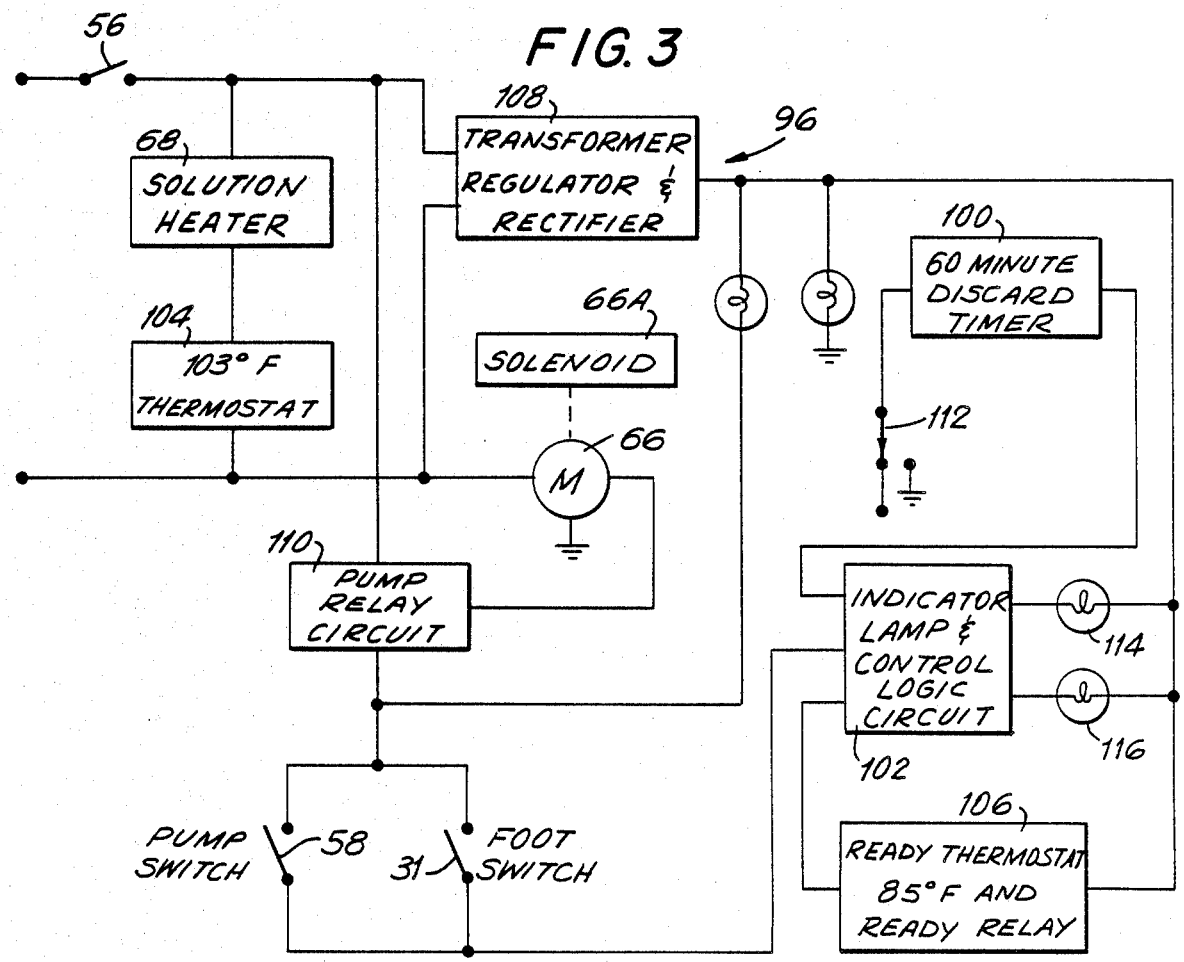
FIG. 3 is an electrical schematic of the overall control arrangement for the power supply for the system of the present invention.
Figure 4:
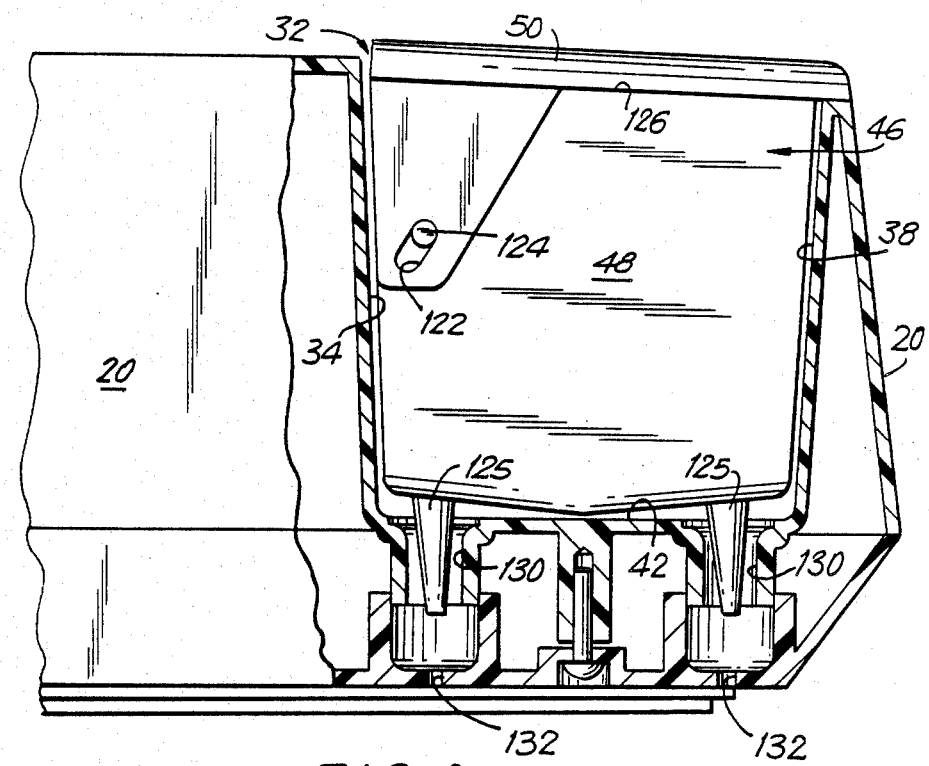
FIG. 4 is a partial sectional view taken through the housing with the reservoir container in place and illustrating the position of the hinge mounting of the reservoir cover with respect to the well defined by the housing and generally along the line 4—4 of FIG. 1.
Figure 5:
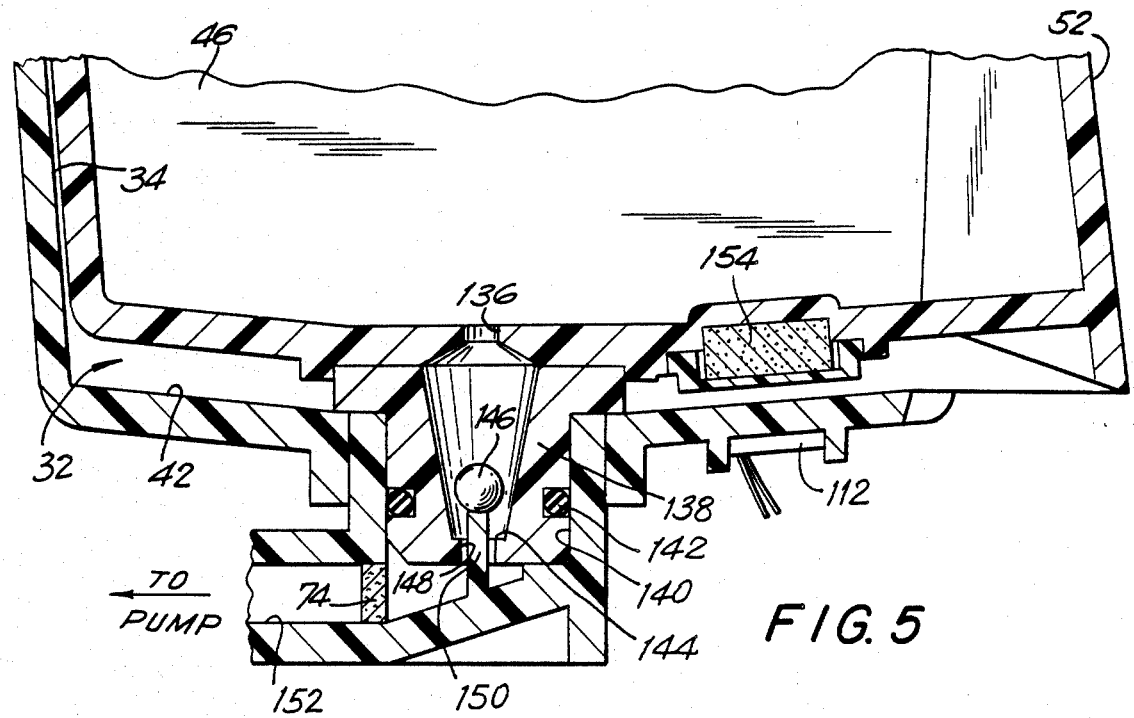
FIG. 5 is a partial sectional view taken generally along the line 5—5 of FIG. 1.

Attention is initially invited to FIGS. 1-3 for a general discussion of the present invention. In this regard, FIG. 1 illustrates a preferred type of apparatus embodying the system of the present invention. FIG. 2 is a mechanical schematic of a preferred form of the invention and also includes several alternative features, namely, alternative types of drives for the pump means, and an additional air pump used with a solenoid drive for the main fluid pump. FIG. 3 is an electrical schematic of one form of control system or circuit for the present invention. Looking to FIG. 1, the apparatus of the present invention is designated generally 20 and includes a housing assembly 22 in which the pumping means, heater means and control means for the overall system are housed. The system of the present invention is electrically powered, and as such there is provided an electrical supply cord 24. Also shown in FIG. 1 is the hand piece 26 which is used to apply the dental treatment solution to the patient and which is connected to the housing and to the pump means interiorly of the housing by a conduit 28. The hand piece 26 includes an applicator tip 30 which is used not only to direct the pulsating jets of the dental treatment solution onto the decayed or carious portion of the tooth, but is also used to scrape away the loosened carious material. Further, the apparatus 20 also includes a foot switch 31 which as will be explained with regard to the electrical schematic of FIG. 3, is used selectively to operate the pumping means. Directing attention to the left hand portion of FIG. 1, it should be noted that the housing 22 includes wall structure which defines a well designated generally 32. The well 32 is formed by four sidewalls 34, 36, 38, 40 and a bottom wall portion 42. The front sidewall 38 is slotted at 44, the slot 44 opening to the front of the housing. A reservoir container 46 is provided which can be removably disposed in the well 32. The container 46 includes a main body portion 48 and a pivotally mounted lid 50. The main body portion 48 has an extension 52 which is transparent and which is disposed in the slotted portion 44 provided by the well 32 when the reservoir container is assembled in the well as is illustrated in FIGS. 4 and 5. The transparent extension 52 can thus be viewed from the exterior of the housing and provides a visual reference as to the level of dental treatment solution remaining in the reservoir container 46. The opening 44 in the housing 22 extends vertically such that the bottom wall of the extension 52 is exposed. Thus, the extension 52 also serves as a finger grip to facilitate removal and placement of the reservoir container 46.

In addition to the above-discussed structure, the housing 22 includes a control panel area 54 which includes a pair of switches 56 and 58. The first of these switches, switch 56 is the power on/off switch, while the other switch 58 is connected and parallel with the foot pedal switch 31, see FIG. 3, and can be used to close the power circuit to the pump drive motor or solenoid. A cover or shield 60 is provided over the control panel area 54 which prevents any spillage that may occur during positioning of the reservoir container 46 from reaching the switch components 56 and 58.

With reference now to FIG. 2, there is shown a general schematic illustration of the overall mechanics of the system of the apparatus 20 of FIG. 1. A preferred system is shown in full line, with certain alternate components being illustrated in dotted or phantom outline. The system basically includes the reservoir 46, a pump arrangement 62; pump drive means 64 in the form of an electric motor 66 or alternately a solenoid 66A; a heater 60A for raising the temperature of the dental treatment solution to approximately the patient's body temperature to avoid patient discomfort, which heater 68 is connected in line with the hand piece 26 by means of the conduit 28. As an alternate arrangement to that as shown in full line, an additional component may be employed in the form of an air pump 70 which is connected downstream of the pump 62 and between said pump 62 and the heater 68. The air pump 70 is used primarily to purge the fluid line leading to the heater 68 and the line 28 from the heater to the hand piece, as well as the hand piece 26, in instances where the efficiency of the pump arrangement 62 is not sufficient to effect both pumping and a purging operation. This point will be discussed in greater detail hereinafter.

The use of the air pump 70 depends to a great extent upon the efficiency of the design of the pump 62. With a pump construction such as that as shown in FIGS. 9-15, coupled with a motor drive, it has been found that the air pump 70 is not necessary. Where a solenoid operated pump such as that shown in FIG. 16 is employed, and the overall design employs relatively inefficient ball type check valves, the use of an air pump 70 to purge the line may be required. In such an instance, it has been found that the ball type check valves are relatively inefficient. Thus, where the pump is not primed, and must in effect pump air initially to become self-priming. With the relatively small volume or stroke of each pump cycle, the ball type check valves cannot effectively operate to produce the required suction to draw dental treatment solution out of the reservoir 46 into the pump, as well as purge the heater 68, conduit 28 and hand piece 26. The pump arrangement as will be discussed in detail with regard to FIGS. 9-15 has been found sufficiently efficient so that not only can it be used to purge the line, but is also self-priming.

Continuing with reference to FIG. 2, the mechanical schematic shown therein will now be discussed in somewhat greater detail. In this regard, the reservoir 46 is connected to the pump 62 by means of a fluid line 72 which is termed the pump inlet line. Disposed in the pump inlet line 72 are a series of filters 74, 76 and 78. The first filter 74 is disposed immediately adjacent the reservoir 46 and is a coarse filter, with filter 76 being an intermediate filter, and filter 78 a fine filter. The series of filters 74-78 serve to filter out any contaminants or solids which may have inadvertently become suspended in the dental treatment solution. These contaminants or impurities not only could be distasteful to the patient, but also could foul the operation of the pump 62, if not removed from the dental treatment solution.

Figure 7:
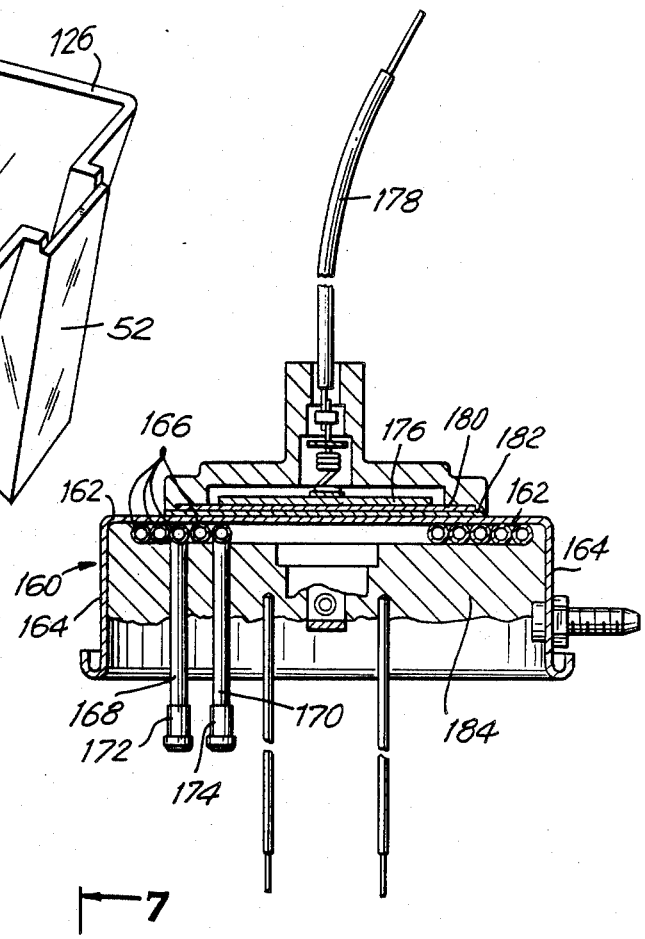
FIG. 7 is a sectional view taken along the line 7—7 of FIG. 8.
Figure 8:
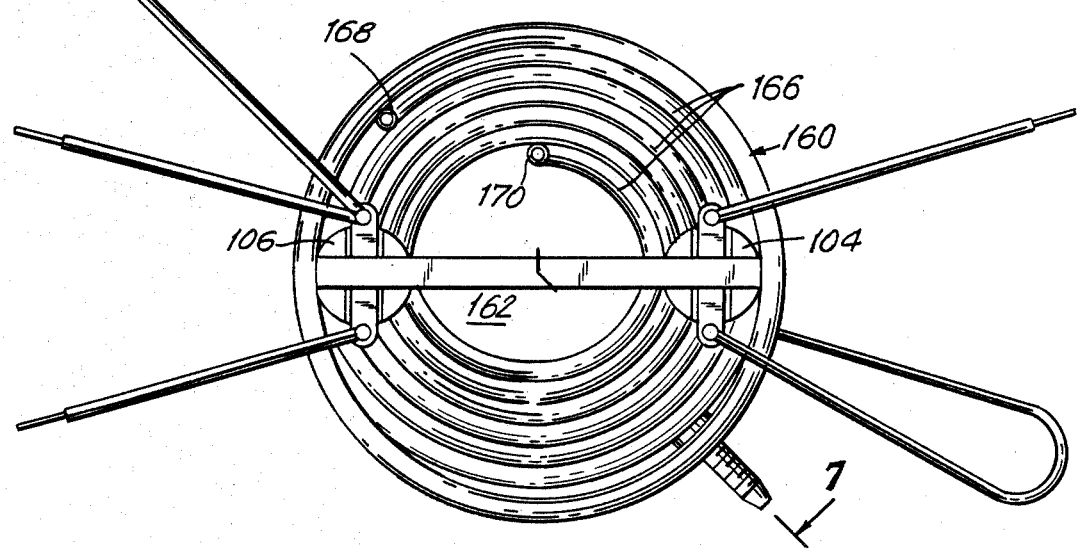
FIG. 8 is a top plan view of the heater of FIG. 7.

It must be stressed at this point, that the illustration in FIG. 2 of the pump 62 is purely schematic. A preferred embodiment or construction for the pump 62 is shown in greater detail in FIGS. 9-15 and a discussion thereof will follow hereinafter. The pump 62 is essentially a diaphragm pump including a pumping chamber 80, a diaphragm 82 disposed within the chamber. The flow of dental treatment solution to and from chamber 80 is controlled by inlet check valve means 84 and an outlet check valve means 86. The prime mover or drive means for the pump is connected directly to the diaphragm to produce reciprocal movement thereof. In this regard, the prime mover may be a motor 66 or alternately a solenoid 66A. The operation of a diaphragm pump is a relatively conventional and well-known one, and as such further description thereof is not deemed necessary at this time. Thus, it is believed apparent from the schematic illustration, that the dental treatment solution 47 will be drawn from the container 46 through the pump 62 and delivered to the fluid line 88 leading to the heater 68. The fluid will pass into the heater, one form of which is shown in FIGS. 7 and 8, wherein the temperature of the dental treatment solution 47 is raised to approximately the body temperature of the patient. The line pressure produced by the pump 62 is sufficient to force the dental treatment solution 47 through the heater, through a final filter 90 and through the conduit 28 for delivery to the hand piece 26.

As mentioned above, it has been found that in certain instances, depending upon the design of the pump 62 it may be necessary to employ a second pumping means 70 for purging the system. More specifically, it should be recalled that the dental treatment solution 47 has a limited usable pot life, approximately one hour. Accordingly, after the pot life has been exhausted and a fresh solution is being prepared and disposed in container 46, or initially preparatory to preparing the system for operation, it is necessary to purge the line 88, the heater 68, line 28 and the hand piece 26. In those instances where the pump 62 is not efficient enough to effect the purging operation, an air pump 70 is employed which is used to force air through the lines thereby expelling any expired dental treatment solution from the above-mentioned components. It should be noted that in addition to the pump 70, the system would then include an air conduit line 92 and a check valve 94, as shown.

A general electrical schematic of the control circuit for the apparatus 20 is shown in FIG. 3 and designated 96, with previously designated components bearing like reference characters. Before reviewing the operation of the pump control circuit in detail, a particular important feature of the system of the present invention should be discussed. As mentioned above, the dental treatment solution has a limited pot life, approximately sixty minutes. Accordingly, the present invention provides means whereby the overall system, and in the present embodiment the pump motor is disabled once the solution pot life is exceeded. In the illustrated embodiment of FIG. 3, this is accomplished by means of a Discard Timer 100 which is connected with an Indicator Lamp Control Logic Circuit illustrated in block form and designated generally 102. The basic operation of these components will now become apparent from a general description of the circuit 96, FIG. 3.

In addition to the components previously discussed such as the power switch 56, pump switch 58, foot switch 31, heater 68 and pump motor 66, the pump control circuit 96 includes a pair of thermostats 104 and 106. The first thermostat 104 is in series with the heater 68 and is set to assure that the heater temperature does not exceed a specified maximum temperature, in this instance 103° F. The second thermostat, 106, is associated with the logic circuit 102 and is termed the Ready Thermostat and is set so that the logic circuit 102 will disable or interrupt the power supply to pump 66 until such time as the temperature of the heater reaches a prescribed minimum, in this instance 85° F. The pump control circuit 96 also includes a Transformer, Regular and Rectifier Circuit illustrated in block form and designed 108, and a Pump Relay circuit 110, also shown in block form and designated 110. Finally, the circuit 96 also includes an additional switch component 112 which is a normally open switch that is operated to the closed condition upon disposition of the reservoir container 46 in the well 32. Operation of the switch to the closed condition will close the circuit to the sixty minute Discard Timer 100, and commenc the timing cycle.

In operation, the switch 56 is initially closed to provide power to the overall circuit arrangement 96. Power is initially supplied directly and will remain applied directly to the heater 68 during the period of time in which the switch 56 is closed. The thermostat 104 controls the maximum temperature attainable by the heater 68 limiting this temperature to approximately 103° F. The closing of the switch 56 will not, however, immediately supply power to the pump motor 66, due to the Logic Control Circuit 102 which, as will be explained, determines when the motor 66 or alternately solenoid 66A may be energized.

Assuming the disposition of a reservoir container 46 in the well 32 with a fresh supply of dental treatment solution, the switch 112 will be closed and the timing cycle for the timer 100 is commenced. At this point, the lamp 114 may be energized to indicate that the timing circuit is commenced, or alternately, the Logic Control Circuit may not energize the lamp 114 until such time as the timer 100 is timed out, thereby providing a visual indication that a fresh supply of dental treatment solution is needed. In addition to the timer 100, the output of the Logic Control Circuit 102 is also controlled by the Ready Thermostat 106 which monitors the temperature of the heater 68, and will not permit an output from the Logic Control Circuit 102, until such time as a minimum temperature level, for example 85° F. is reached. Thus, once the switch 112 is closed and the basic minimum temperature is reached at the heater 68, the motor 66 or alternately solenoid 66A may be energized through either the pump switch 58 or the foot switch 31 which are disposed in parallel, and jointly in series with the motor 66 or solenoid 66A. The closing of the pump switch 58 will provide for continuous operation of the motor 66, while the foot switch 31 is useful in that the dentist may attain intermittent operation of pump 62 as needed.

Thus, it may be appreciated that before the pump motor 66 or solenoid 66A can be operated a number of events must occur, first heater 68 must reach a prescribed minumum temperature and a reservoir container 46 must be disposed in the well 32 in its presence sense or determined by the closing of the switch 112. In the preferred embodiment of the invention as illustrated in FIG. 5, the switch 112 is a proximity switch which will be operated by a magnet carried by the reservoir container 46. It is also contemplated, that a mechanical switching arrangement may also be utilized which will be operated by disposition of one of the support legs for the reservoir container in an opening in the bottom wall 42 of the well, a structural arrangement which can be appreciated from the viewing of FIG. 4. Thus, when switch 112 has been closed and the desired temperature reached the pump can be energized either through the pump switch 58 or the foot switch 31. Further, once the timer 100 has timed out, the power supply to the pump motor 66 or alternately solenoid 66A will be interrupted, as the timing out timer 100 will interrupt the output from the Logic Control Circuit 102 with the lamp 114 being either energized or de-energized, as the case may be to provide the dentist with an indication that a fresh supply of dental treatment solution must be prepared.

Attention is now directed to certain of the structural features of the components which serve to make up the system and apparatus 20 of the present invention. In this regard, the construction of the reservoir container 46 will initially be considered with regard to FIGS. 4-6.

The reservoir container 46, as mentioned previously, includes a body portion 48 and a lid 50. FIG. 4 is a partial sectional view showing the reservoir container 46 positioned in the housing well 32. This sectional view is taken adjacent the left hand portion of the well 32 and generally along the lines 4—4 as indicated in FIG. 1. As such, only the housing 20 is shown in section, the container being shown in full line. The cover member 50 for the container 46 includes a pair of side flanges 120, only one of which can be viewed in FIGS. 4 and 6 which side flanges embrace the opposite sides of the body 48. Each side flange 120 includes an elongate pivot slot 122, while the body 48 is provided with a pair of corresponding pivot pins or posts 124 disposed in the pivot slots 122. In addition, it should also be noted that the container body 48 also includes a number of support posts or legs 125 which extend from the bottom wall portion thereof.

In the assembled condition of FIG. 4, it will be noted that while the pivot arranqement 122-124 will permit the cover member 50 to be opened, opening cannot occur when the reservoir container 46 is disposed in the well 32. More specifically, it will be seen that the pivot point for the lid 50 defined by the pivot pins 124 is positioned well below the rim 126 of the container body portion 48, such that in the assembled condition this pivot point is also disposed relatively inwardly of the well 32. Thus, any attempt to open the cover 150 will be impeded or prevented by engagement of the cover with the well surface wall portion 34. In order for the container 46 to be opened, it must first be removed from the well portion 32, thereby the addition of dental treatment solution to a previously mixed batch within the well is effectively discouraged.

Figure 6:
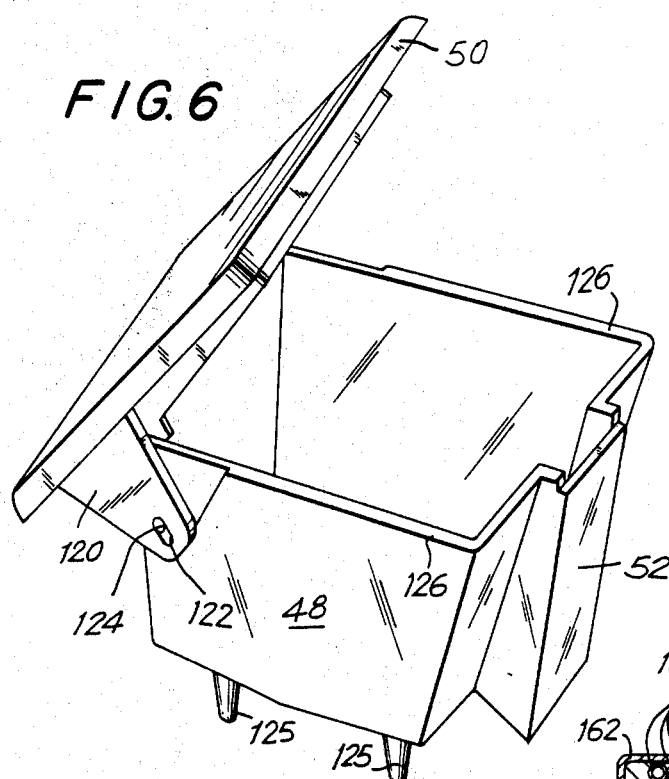
FIG. 6 is a perspective view of the reservoir container of the present invention with the lid thereof in a partially open or intermediate position.

With reference to FIG. 6, it should be noted that the cover 50 also includes a pair of detents 128, only one of said detents 128 being shown in FIG. 6. It should be understood, however, that a similar detent 126 is provided adjacent the flange 120 on the opposite portion thereof, both said detents being spaced inwardly from the flanges 120 so that when the cover 50 is in the closed position, the detents are disposed interiorly of the body 48. With the detents 128, the container 46 can be removed and the lid opened to an intermediate position as shown in FIG. 6, with the detents 128 engaged upon the rim 126 to hold the lid in the intermediate position for filling of the reservoir container. In this instance the pins 124 are disposed in the upper regions of the slot 122 and the reservoir container is in a relatively balanced condition. The cover 50 may be moved to a fully opened position (not shown) by utilization of the slotted pivotal connections, and a lifting of the cover slightly to effect a lateral movement to disengage the detents 128 from the rim 126 and thereby permit the cover to be moved to a fully opened position if so desired.

Also viewable in FIG. 6, is the extension 52 on the front wall portion of the body 48. You will recall that this extension 52 is transparent, and is received within the slotted wall portion 44 so that it may be viewed from the exterior of the housing once the reservoir container 46 is assembled with the remainder of the housing 22. The extension 52 also provides means whereby the container can be removed from the reservoir well 32.

Attention is again directed to FIG. 4, where it can be seen that the bottom wall portion 42 of the well 32 is provided with a series of openings 130 which will accommodate the legs or support post 125 for the reservoir container. The openings 130 are considerably oversized with respect to the legs 125 and communicate directly with additional openings 132 in the bottom portion of the housing 22. As such, the openings 130 and 132 in effect provide drain means for the well 32. Thus, should any spillage occur upon placement or removal of the reservoir container 46, the spilled dental treatment solution will drain out the bottom of the housing, there being no danger that leakage might occur interiorly of the housing which might short-circuit the electrical components.

FIG. 5 is a sectional view taken generally along the line 5—5 of FIG. 1 and generally centrally of the reservoir container 46. This view illustrates additional structural features of not only the reservoir container 46, but also of the well portion 32 of the overall housing construction 22. Looking first to the reservoir container 46, the bottom wall portion 134 includes a discharge opening 136 and a valve nipple or housing 138 which is affixed to the outer portion of the bottom wall 134. The valve housing 138 is received within a recess 140 provided in the bottom wall 42 of the overall well portion, and as will be noted, the exterior of the housing 138 is provided with an O-ring seal 142 which will engage the wall surface of the recess 140. Further, the housing 138 includes an interior valve seat 144 and a ball check valve member 146. Thus, when the reservoir container 146 is removed from the well 32 and filled with fluid, the pressure created by the head of fluid or liquid in the reservoir container, will force the ball 146 down against seat 144 thereby sealing the exit opening 148 from said housing. The well portion 32 includes means for unseating the ball check valve 136 when the container 46 is positioned therein, said means is in the form of a post 150 which upon disposition of the valve housing 138 within the recess 140 will enter the discharge opening 148 and bias the ball 146 upwardly as shown in FIG. 5. The dimension of the post 150 is such that the dental treatment solution can flow around the post and into the passageway 152 provided in the housing 22 also, it should be noted that a coarse filter 74, discussed previously, is provided in the conduit 152 for effecting the initial filtering operation of the dental treatment solution.

The bottom wall 42 of the well portion 32 also includes a proximity switch 112 as discussed with respect to circuit 96 of FIG. 3, which switch 112 is in circuit with the timer 100. Correspondingly, the reservoir container 46 includes a magnet member 154 which when the reservoir container 46 is positioned as shown, will operate the proximity switch 112 to a closed position thereby energizing the timer 100 as discussed previously with respect to the overall control circuit 96.

Before discussing the pump arrangement of the present invention as shown in FIGS. 9-15, attention is directed to the novel heater assembly used to bring the dental treatment solution up to body temperature. The heater unit it will be recalled, was previously designated 68, FIG. 2, and details thereof are shown in FIGS. 7 and 8, wherein FIG. 7 is a sectional view of the complete unit, after a potting compound has been introduced into the main body portion thereof, while FIG. 8 is a top plan view of the unit prior to the addition of the potting compound.

With reference to the above-mentioned FIGS. 7 and 8, the heater unit 68 basically includes a cup-shaped body portion 160 which defines a base wall 162 and a generally circular sidewall 164. A spirally coiled section of tubing 166 is disposed within the body portion and is in engagement with the base wall 162 as shown in FIG. 7. The coiled section of tubing includes an inlet portion 168 and an outlet portion 170 disposed generally transverse to the spirally coiled portion and extending upwardly and out of the body portion 160. The respective inlet and outlet portions include end nipples 172 and 174 for attachment to additional sections of tubing leading from the pump mechanism and to the hand piece, respectively.

While the type of heat generating means for the heater assembly 68 is not a critical feature of the present invention, in a preferred form, however, a positive temperature control device 176 (PTC) is positioned in association with the side of the bottom wall 62 opposite the section of coiled tubing 166. The PTC device is a commonly used element in heater arrangements and basically is designed such that resistance to current flow increases as the temperature of the device increases and thus the unit is essentially self regulating in that it will tend to reach a maximum temperature and remain at that temperature. PTC devices are well-known and readily available, and as such a further description of the properties thereof is not deemed necessary. It should be noted, however, that electrical lead 178 is provided which is connected to the PTC device as a source of energizing current, the device being energized when switch 56 is closed.

In the illustrated embodiment, the PTC device 176 is not disposed immediately adjacent to the wall 162, rather, a pair of heat transfer plates 180 and 182 are employed which will tend to distribute the heat generated by the PTC device 176 evenly over the base wall 162. The heat from the base wall 162 then is transmitted to the coil tubing 166 and correspondingly to the dental treatment solution 47 flowing therethrough.

As was mentioned previously with respect to the electrical circuit 96 of FIG. 3, the heater is monitored by two thermostats 104 and 106. These thermostats are shown in FIG. 8, as are the circuit leads which are attached thereto. Basically, the thermostats 104 and 106 are placed in close proximity or association with the section of coiled tubing 166 and as such can monitor the temperature of the dental solution in said tubing.

The construction of the heater 68 is completed by the addition of the potting compound 184 which will partially fill the cup-shaped body portion 160, while completely covering the spirally coiled section of tubing 166, except for the inlet and outlet portions 168 and 170. This arrangement is shown in detail in FIG. 7. It also should be noted that the various leads for the thermostats 106 and 104 will also extend exteriorly of the potting compound 184.

Figure 9:
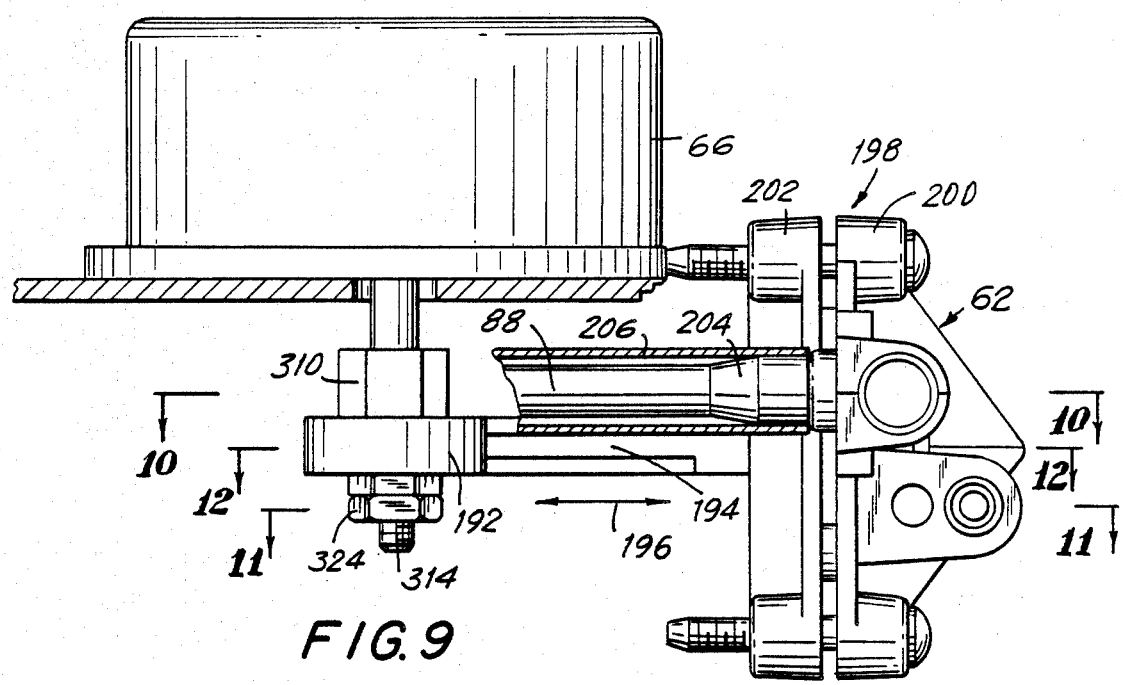
FIG. 9 is an elevational view of the improved pumping arrangement of the present invention.

Attention is now directed to FIGS. 9-15 wherein a detailed illustration of the preferred design of the pump arranqement 62 and its drive mechanism 66 is illustrated in detail. FIG. 9 is an illustration in elevation of the overall pump arrangement 62, as well as the drive motor which is utilized to provide the rectilinear movement of the diaphragm member. As can be noted, three sectional views are taken with respect to FIG. 9 along the lines 10—10; 11—11; and 12—12. The overall construction of the pump arrangement will best be understood with reference to these sectional views which will be discussed in greater detail hereinafter in conjunction with FIG. 9.

Basically, the arrangement for the pump and pump drive means as shown in FIG. 9 includes the drive motor 66 which has an output shaft 190, which is coupled to an eccentric crank arrangement, FIG. 14, which is in turn coupled to a crank collar 192 and a crank arm 194, the later is attached to the diaphragm. The crank arm 194 is operated rectilinearly in a reciprocating motion as indicated by the arrow 196 and this produces the flexing or required movement of the diaphragm necessary to attain the pumping action. The pump, per se, as shown in FIG. 9 is designated generally 62 in accordance with the prior discussion. The pump 62 has an overall housing construction 198 which is comprised of housing components 200 and 202 which can be appreciated in greater detail with respect to the sectional views of FIGS. 10-12 to be discussed hereinafter. Also viewable in FIG. 9 is the outlet port for the pump 62 which is designated 204 which is coupled to a conduit 88 leading to the heater means, and in this regard, reference is had to the discussion with respect to FIG. 2. One important feature of the present invention, is the fact that a cover or shield is provided over all of the internal tubing, the shielding tube or cover is designated 206 in FIG. 9, and tube 206 shields the outlet conduit 88 against any leakage. Should a pin hole leak in the tubing occur, this could result in a stream of dental treatment solution arcing over to one of the electrical components which could then create an electrical circuit path through the dental treatment solution to the patient thereby causing discomfort and possible harm. The employment of the shields 206 over the internal tubing throughout the interior of the unit 22 guards against any leakage and short-circuiting of this nature.

Figure 12:
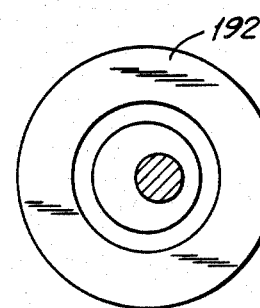
Figure 12:
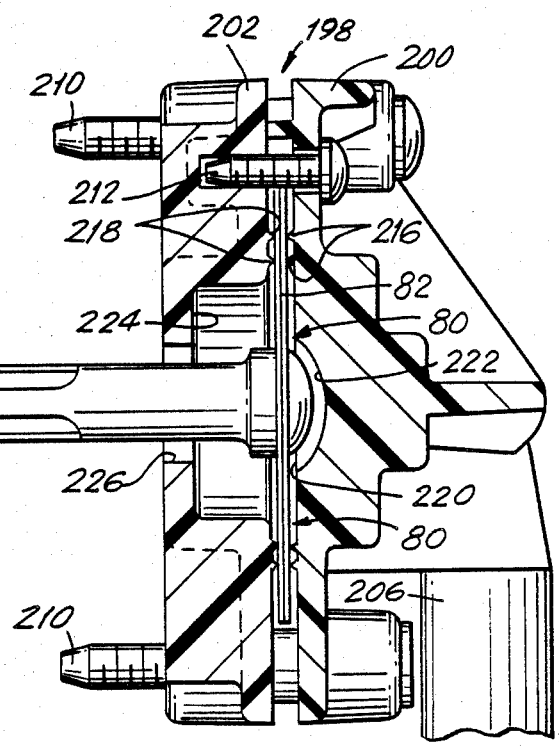

The basic construction of the pump 62, as well as the drive means components which are employed to operate the pump are probably best shown in FIG. 12, which figure is a sectional view approximately on the center line of the pump 62. The pump housing assembly 198 is comprised of a pair of facing housing sections 200 and 202 which are held in clamped engagement by peripheral fasteners 210, as well as additional fastener elements 212 as needed. Respective housing sections include facing raised ribs 216 and 218 on the inner surfaces thereof which engage and clamp the peripheral surface of the flexible diaphragm member 82 positioned therebetween. The ribs are circumferentially continuous, and thus provide a seal about the periphery of the diaphragm member 18. The facing surface of the housing section 200 is relieved in the area of the diaphragm, as indicated at 220 to define a portion of the pumping chamber 80, and also at 222 to accommodate the enlarged head of the fastener used to affix the diaphragm to the crank arm 194. These surfaces 220 and 222, thus cooperate with the diaphragm 82 to define portions of the pumping chamber 80. The mating housing section 202 is relieved in the area 224 to accommodate flexing of the diaphragm 82 as required, and is also apertured at 226 to permit the crank arm 194 to enter the housing for connection to the diaphragm. Accordingly, the pump chamber which is designated generally 80 is essentially defined by the surfaces 220 and 222 of the housing section 200, and the interior portion of the flexible diaphragm 82 disposed radially inward of the clamped areas at projections 216 and 218. The volume of the chamber 228 and correspondingly the volume of liquid to be pumped will vary depending upon the relative position of the flexible diaphragm 82 at the beginning and end of each reciprocal pump stroke. As will be discussed in greater detail hereinafter, the pump arrangement 62 of the present invention includes means for selectively adjusting the stroke of the crank arm 194, and correspondingly the stroke of diaphragm 82 and the amount of liquid to be delivered with each pump stroke.

Figure 10:
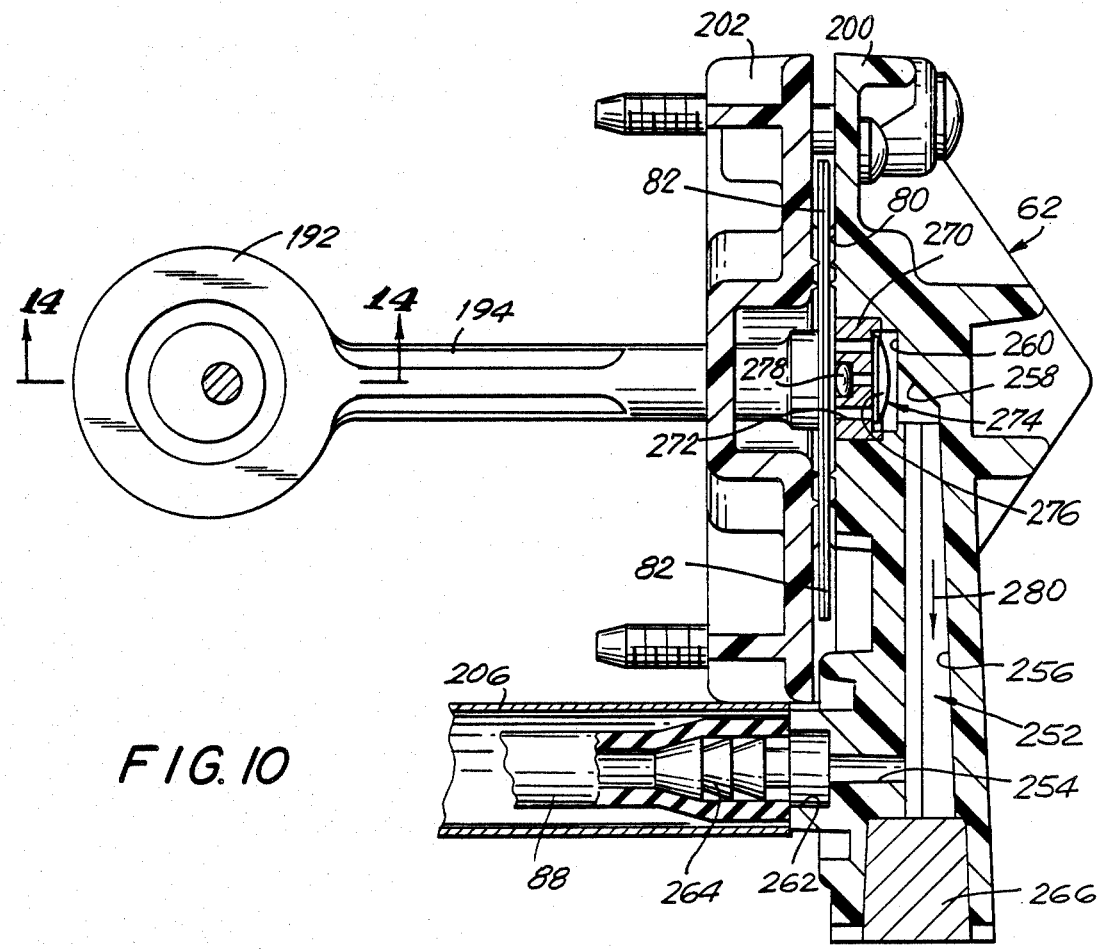
FIGS. 10-12 are sectional views taken along the lines 10—10; 11—11; and 12—12, respectively of FIG. 9.
Figure 11:
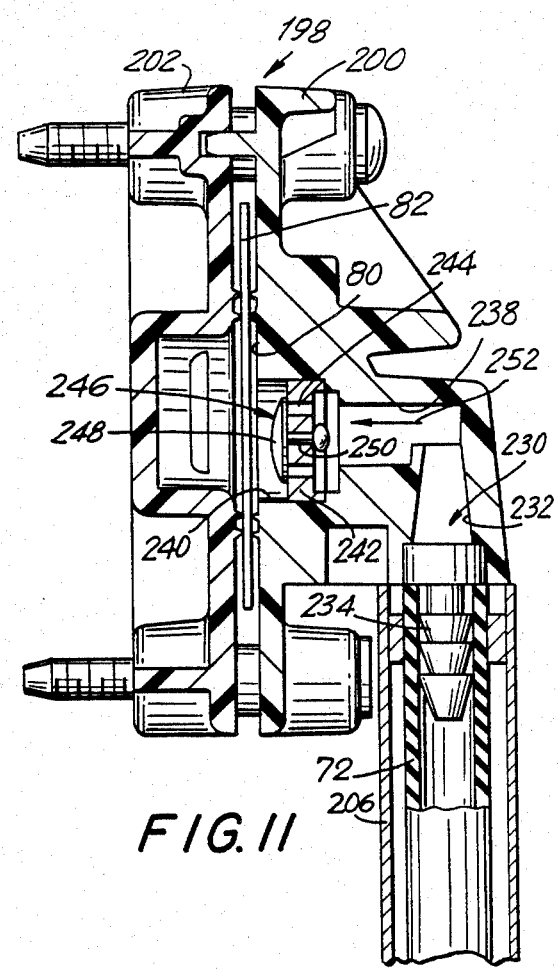

In FIGS. 10 and 11, a preferred form of design for the pump check valves is illustrated. More specifically, FIGS. 10 and 11 are sectional views through the pump 62 taken along the center line of the outlet and inlet passages respectively. In this regard, it will be noted that both the inlet and outlet passages, as well as the associated check valves are carried by the housing section 200.

Initially, attention is directed to FIG. 11 which illustrates the construction of the inlet passage in the housing section 200 leading to the pump chamber 80. This inlet passage is designated generally 230 and includes a first portion 232 open into the exterior of the housing and associated with a connector 234 which is in turn coupled with the delivery line 72 leading from the reservoir container 46. The line 72 is shielded by tubular jacket 206 in a manner similar to that as previously discussed with regard to FIG. 9. The passage 230 further includes a second portion 238 which is disposed transverse to and intersects the section or portion 232. This transverse passageway section 238 opens into the pump chamber 80 through an enlarged valve chamber 240. Disposed in the valve chamber 240 is an insert member 242 which is provided with a series of apertures 244, and carries a flexible diaphragm type check valve 246. The diaphragm valve 246 includes a conical shaped portion 248 which overlies the apertures 244, and a stem 250 which is received through an additional aperture formed in the insert member and includes a bulbous portion to maintain the overall valve member 246 in position. Thus, when fluid is flowing in the direction as indicated by the arrow 252 the conical portion 248 will be unseated and liquid is permitted to enter the pump chamber 80. Reverse flow is, however, prevented as reverse flow will force the umbrella or conical shaped portion 248 into engagement with the surface of the insert 242 thereby covering and sealing the apertures 244. Thus it can be seen, that the valving arrangement as illustrated provides an effective one way type check valve, that will react quickly to small changes in liquid flow.

Looking now to FIG. 10, the outlet pessageway for the pump 62, as well as the outlet check valve is illustrated. More specifically, the pump housing section 200 is provided with a series of bores 254, 256 and 258 which lead from the exterior of the housing to a valve chamber 260. The bore 254 includes a counterbore section 262 in which a connector member 264 is provided, which connector member is coupled to the end of the conduit 88 leading from the pump to the heater 68 Here again, the tubular shielding 206 is illustrated surrounding the tube 88. Also, it will be noted that the end of the bore 256 will be closed with a plug 266. Disposed in the valve chamber 260 is an insert 270 similar to the insert 242 discussed previously. The insert 270 includes a series of apertures 272 formed therein which provide for communication from the valve chamber to the pump chamber 80. The insert 270 carries a valve member 274 comprised of a conical section 276 and a stem 278. The conical section 276 will overlie the apertures 272 while the stem 278 includes a bulbous portion which will retain the valving member 274 in position with respect to the insert 270. Thus, when fluid is flowing in the outlet passageway in the direction as indicated by the azrow 280, the fluid will unseat the conical portion 276 thereby permitting the passage of fluid through the ports 272. Any attempt of fluid to move in the opposite direction, as which would occur upon the retraction stroke of the diaphragm, the conical portion 276 will be pulled down into close engagement with the insert covering the ports 272 and preventing reverse flow.

Figure 13:
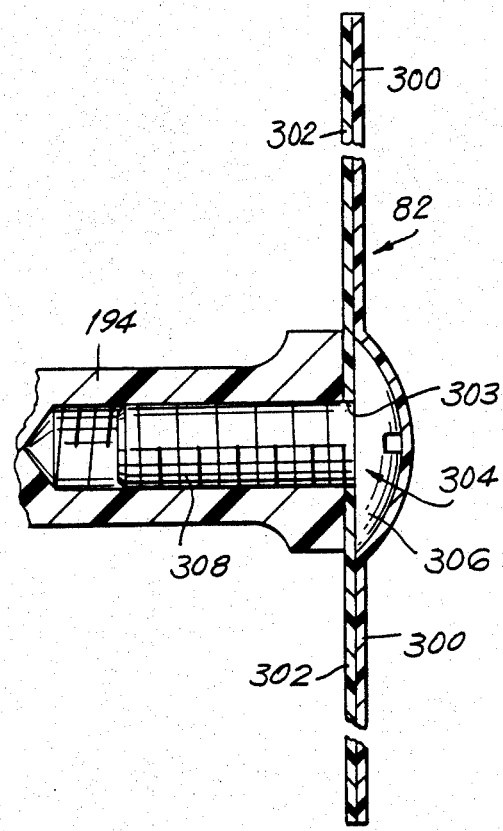
FIG. 13 is a partial sectional view taken through the diaphragm of the improved pumping arrangement of FIGS. 9-12.

FIG. 13 illustrates a preferred construction for the diaphragm 82. In this regard, the diaphragm is provided by a multilayer assembly including a first or inner layer 300 which will be in communication with the dental treatment solution on the interior of the pumping chamber. This layer 300 is preferably formed from Teflon or some other similar material which will not react with the dental treatment solution and is of a nontoxic nature. The outer layer 302 which is bonded to the layer 300 is formed of an elastomeric material, and includes an aperture 303 to accommodate a fastener member 304. The fastener member 304 includes an enlarged head portion 306 and a threaded shank 308, the shank 308 extending through the aperture 303 for connecting the diaphram to the crank arm 194. As can be seen, the inner layer 300 completely covers the enlarged head portion 306 so that the dental treatment solution cannot react with the metal fastener member. Thus, it can be seen that the head 306 of the metal fastener is in effect encapsulated by the inner layer 300 and the outer layer 302, except for the shank portion 308 which extends therefrom.

Figure 14:
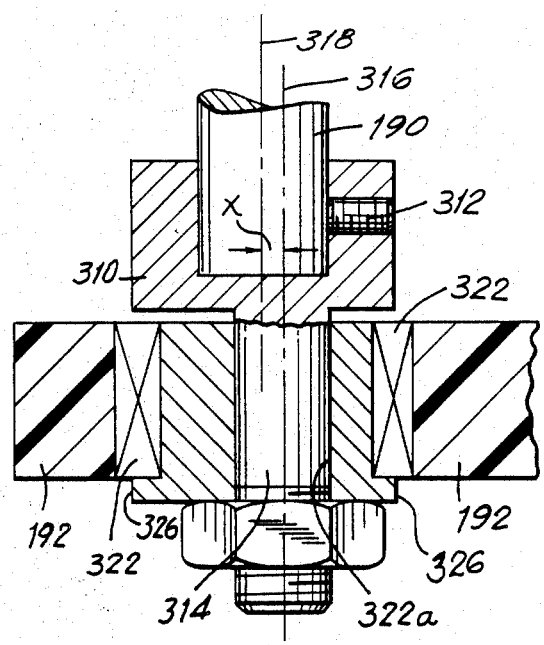
FIG. 14 is a view taken partially in section, along the line 14—14 of FIG. 10 and illustrating the eccentric adjusting means for the pump crank arm.
Figure 15:
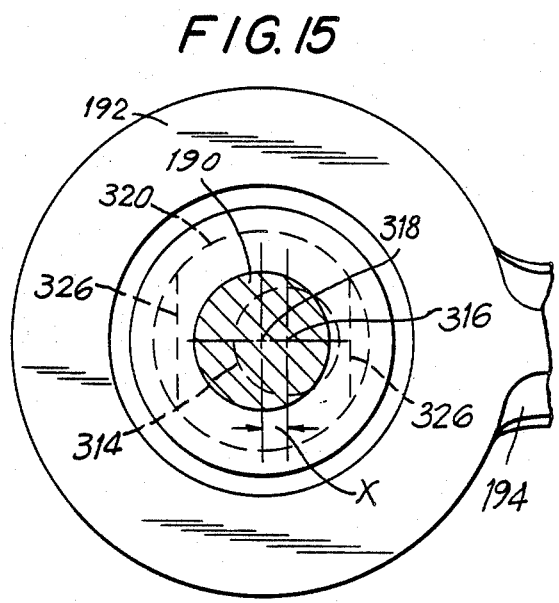
FIG. 15 is a plan view of the crank arm collar and adjustment means of FIG. 14.
Figure 16:
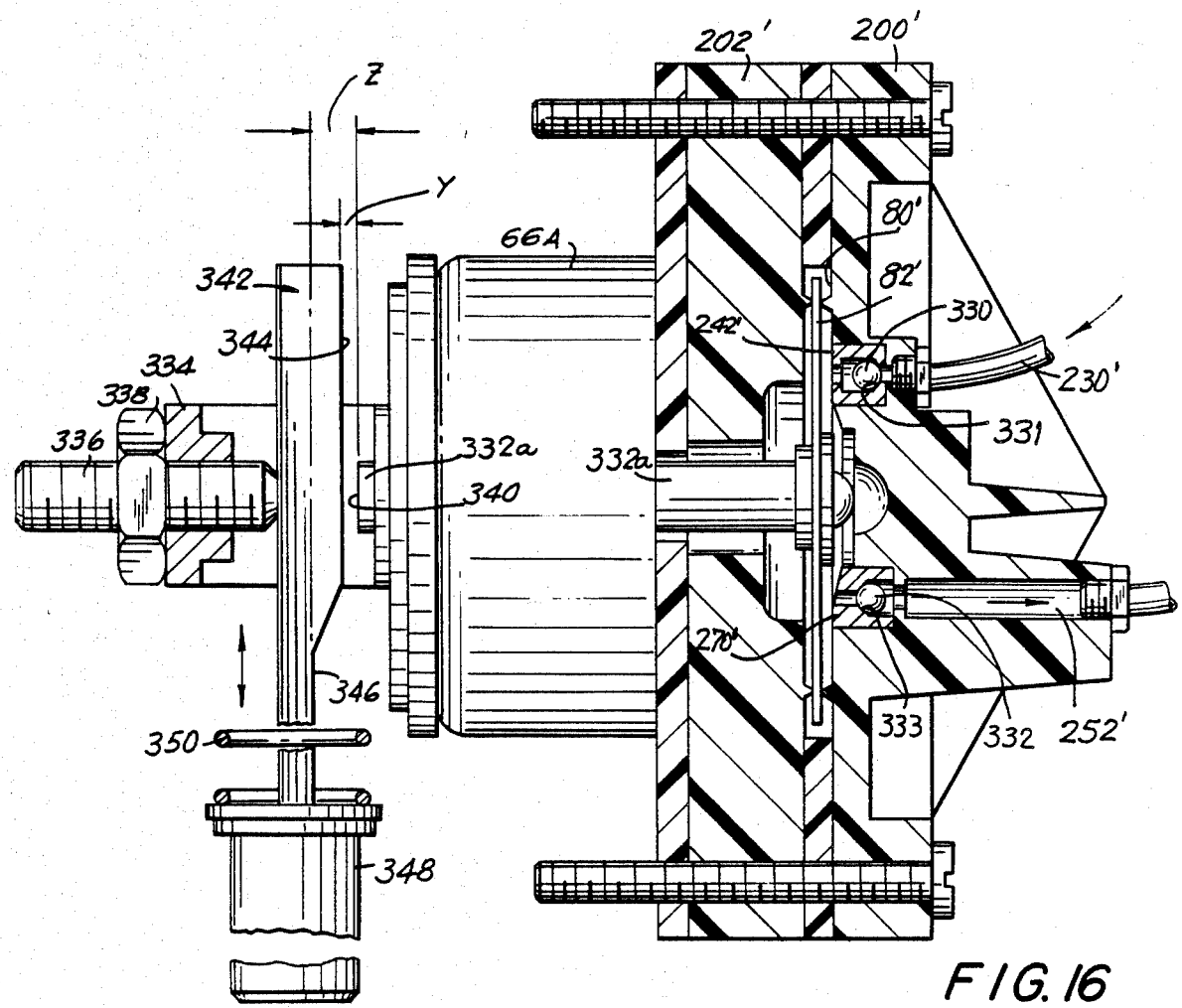
FIG. 16 is a partial sectional view illustrating an alternate pumping arrangement from that illustrated in FIGS. 9-15.

The means for adjusting the receptacle stroke of the diaphragm 82 and correspondingly the volume of liquid dispensed by the pump 62 with each pulsating jet or instance of flexing of the diaphragm will now be considered with respect to FIGS. 14 and 15. FIG. 14 is a sectional view taken along the line 14—14 of FIG. 10 and illustrating the structure for connecting the motor output shaft 190 to the crank collar 192 and correspondingly the crank aim 194. In this regard, there is provided a cap member 310 which is affixed to the motor output shaft 190 by access screw 312. The cap member includes an eccentrically mounted crank pin 314 which has its center line 316 offset from the center line 318 of the output shaft by distance X. In the drawings, it should be noted that the degree of eccentricity has been exaqgerated for illustrative purposes, as in practice the offset is on the order of 0.010 inches.

The crank pin 314 is received within an adjustment ring 320 which is journaled or rotatably mounted by a bearing arrangement 322 to the crank collar 192. The adjustment ring 320 includes an aperture 322a in which the eccentric crank pin 314 is disposed. It should be noted here, that the aperture 322a is also eccentric with respect to the central axis of the ring 320 which in the position as illustrated in FIG. 14, corresponds to the axis 318 of the motor output shaft. A lock nut 324 is threaded on the end of the crank pin 314 which will effectively lock the adjustment ring 320 in a preselected position. It should be noted further, that the adjustment ring 320 is provided with a pair of diametrically opposed flat tool engaging portions designated 326, FIG. 15, which will permit the relative rotative position of the ring 320 to be adjusted as desired.

Accordingly, with the parts as positioned in FIGS. 14 and 15, that is where the axis of the eccentric aperture 322a coincides with that of the crank pin 14, the effect of stroke of the reciprocating crank on 194 and of the diaphragm 82 will be approximately the degree of offset X as illustrated. The adjustment ring 320 can be rotated, however, to obtain adjustment in the effective length of the stroke. More specifically as the ring 320 is rotated, the position of the crank collar 192 relative to the crank pin will be shifted laterally, to the right or left as viewed and this alters the starting as well as the ending position for the reciprocal stroke of the crank arm 94 and thus in effect decreases or increases the length of said stroke and correspondingly the volume of dental treatment solution which will be expelled from the pump chamber 80 upon each flexing of the diaphragm. It will be recalled, that the pump is designed to provide an intermittent or pulsating stream with the volume of each pulse being controlled to some extent by the relative position of the adjustment ring 320.

Inviting attention now to FIG. 16, there is illustrated an alternative type of pump arrangement from that as shown in FIGS. 9–12. The pump arrangement shown in FIG. 16 is designated generally 62', and while sufficient for the purposes of the present invention, it is not as efficient as the pump design previously discussed. As such, when a design as per FIG. 16 is employed, it is expected that an additional air pump 70 will have to be used in order to effect purging of the system. The pump design 62', however is effective for attaining the desired mode of operation, and constitutes a less expensive pumping arrangement.

More specifically, the pump design includes a pair of opposed housing sections 200' and 202' which operate to clamp a diaphragm 82' to define a pumping chamber 80'. The housing section 200' includes an inlet passage 230' and an outlet passage 230' and an outlet passage 252'. Each of the respective passages communicate with the pumping chamber 80' through a valve chamber in which an insert is mounted carrying a ball type check valve 330 and 332, respectively. Both of the inserts 242' and 270' are provided with valve seats 331 and 333 such that the ball valves will permit flow through the inserts in but a single direction. In this respect, the operation of the pump is essentially the same as that of FIGS. 9–12, however the ball type check valves 330 and 332 are not as efficient as the flexible check valves 246 and 274 of the pump 62.

In addition to the check valve arrangements the pumping system 62' also differs in the prime mover for effecting flexing of the diaphragm. In this regard, in place of the motor 66 with its eccentric crank pin 314, there is provided a solenoid 66A having its armature 322a fixed to the diaphragm 82'. The control circuit will be designed such that the coil of the solenoid is alternately energized to produce a reciprocating motion of the armature 332a as necessary to effect the desired pumping action. The stroke of the armature 332a is controlled by the structure to the left of FIG. 16 as viewed. In this regard, the solenoid 66A includes an extension or arm 334 to which there is attached an adjustably mounted set screw 336 held in position by lock nut 338. Disposed intermediate the set screw 336 and the end of the armature designated 340 is a slide bar or cam bar 342. As shown, the slide bar 342 includes a first surface portion 344 which is spaced from the end 340 of the armature to a distance Y. This distance in the position as shown will effectively control the stroke of the armature 332a and correspondingly the degree of deflection of the diaphragm.

With a pump design such as that of FIG. 16, difficulty has been encountered in priming the pump once the pump runs dry. To overcome this problem, the slide bar 344 was devised, which it will be noted also includes a second portion 346. The slide bar 344 is spring biased so that its normal position is that as shown in FIG. 16. When it is desired to prime the pump, the button 348 is depressed compressing the spring 350 and moving the slide bar portion 346 into position between the set screw 336 and the end 340 of the armature. In this condition, the effective stroke of the armature 332a will now be a distance Z with the increase stroke having been found to effectively attain the desired priming action for the pump 62'. The slide bar 342 is sufficiently flexible in its overall mounting, such that the distances Y and Z can be varied depending upon the position of the set screw 336. Thus, by moving the set screw 336 forward or backwards, the volume of each pulse of dental treatment solution expelled by the pump 62' can be controlled, and this can be done without effecting the ability of the slide bar 342 to enable the pump to be primed when necessary.

Figure 17:
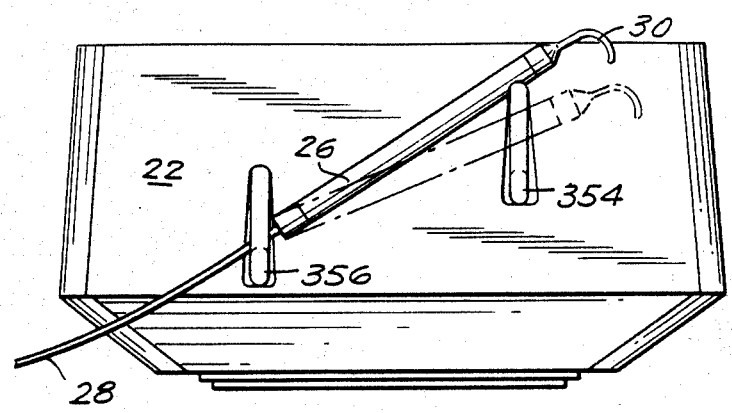
FIGS. 17 and 18 illustrate an improved storage and holding arrangement for a dental hand piece incorporated with the housing arrangement of the present invention.
Figure 18:
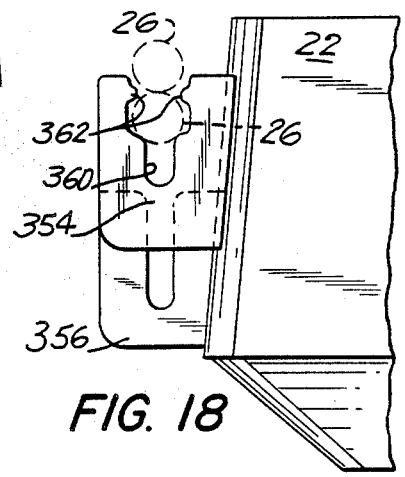

FIGS. 17 and 18, illustrate the means provided for accommodating the hand piece 26 when not in use. In this regard, the housing 22 includes a pair of bracket members 354 and 356 mounted to one side thereof. The bracket members are generally U-shaped, with the bracket 356 including a slot of sufficient size to accommodate the conduit 28 leading to the hand piece. The bracket 354, as can be seen in FIG. 18, includes a somewhat wider slot for accommodating the hand piece. The slot includes a pair of detent members 362 which will permit the hand piece to rest on the exterior of the bracket, or permit the hand piece to be snapped past the detents and received in the lower regions of the slot, as illustrated in dotted outline.

Figure 19:
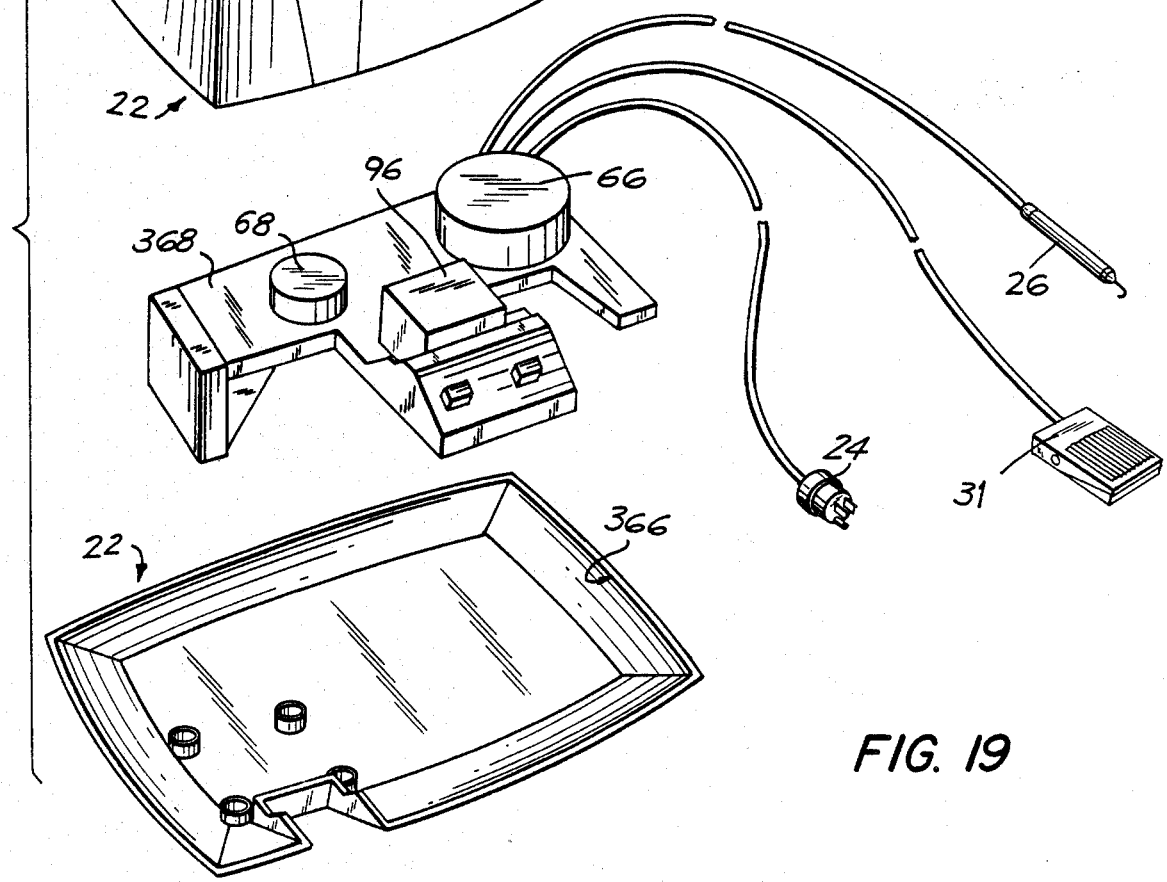
FIG. 19 is an exploded partially perspective view, also shown partially schematically, illustrating a construction and method of assembly of the housing and working components of the present invention.

In FIG. 19, there is illustrated a preferred method of constructing the overall apparatus 20 of the present invention. In this regard, the apparatus is fabricated such that the housing 22 includes an upper housing section 364 and a lower housing section 366. All of the mechanical components of the system, the pump motor 66, the diaphragm pump 62, the heater 68 and the circuit boards which provide the control circuitry are preliminarily assembled to a chassis 368, and extending from the chassis 368 is the power cord 24, foot switch 31, as well as the conduit 28 to which the hand piece 26 is attached. Thus, upon final assembly it is only necessary for the chassis 368 to be affixed to the upper or lower housing sections, in this case the upper housing section 364 and the remaining housing section bolted in place. This arrangement facilitates assembly as the components can be assembled directly to the chassis 368, and it is not necessary that they be fitted within either the upper or lower housing sections 364, 366 until final assembly.

It is thus believed that the overall objects of the invention are fully and effectively realized with the apparatus as illustrated in the drawings and discussed above. The specific embodiment shown and described has been presented for purposes of illustrating the functional and structural principals of the invention, and may be subject to change without departure from said principals. It is envisioned, that those skilled in the art once possessed of the present disclosure, may readily devize various modifications or alternative embodiments without departing from the true spirit and scope of the present invention, as defined by the claims appended hereto.

The invention is claimed as follows:

1. Appartus for delivery of a dental treatment solution or the like, to a patient said apparatus comprising: a housing, pump means and control means for said pump means disposed within said housing, said housing including wall structure defining a well portion, a reservoir container for the dental treatment solution disposable within said well portion, said control means including means for sensing the positioning of the reservoir container in said well, and logic circuit means for disabling the supply of dental treatment solution upon the elapse of a prescribed period of time after the reservoir is positioned in said well.

2. Apparatus according to claim 1, further including heating means for heating the dental treatment solution prior to delivery thereof to a patient, said control means further including thermostat means coupled to said logic circuit means such that the supply of dental treatment solution is prevented until the solution has reached a prescribed temperature.

3. Apparatus according to claim 1, wherein said reservoir container includes a bottom wall structure and valve means carried by said bottom wall structure, said housing including conduit means leading to said pump means and valve actuating means for engaging and opening said valve means upon disposition of said reservoir container in said well portion.

4. Apparatus according to claim 3 and further including filter means disposed in said conduit line comprised of a first coarse filter, a second intermediate filter, and a third fine filter.

5. Apparatus according to claim 1, wherein said means for sensing the positioning of the reservoir in the well comprises a proximity switch carried by the housing and magnet means carried by said reservoir container for actuating said proximity switch.

6. Apparatus according to claim 1, wherein said reservoir container includes a lid pivotally mounted thereto, said lid pivot point being disposed sufficiently below the upper level of said reservoir container such that when said reservoir container is positioned in said well, the wall structure of said well inhibits opening movement of said lid.

7. Apparatus according to claim 1, wherein said housing well wall structure includes an elongate opening extending to the front of said housing, and said reservoir container includes a transparent extension portion received in said elongate well opening and viewable from the exterior of said housing to provide for visual inspection of the level of treatment solution in said reservoir container.

8. Apparatus according to claim 7, wherein said housing further includes a relieved portion adjacent and beneath said elongate housing opening to provide a finger grip whereby said reservoir may be gripped by said extension and removed from said well.

9. Apparatus according to claim 1, wherein said control means includes one or more push button switches mounted to said housing, said switches being mounted in a recess portion of the housing and covered by a housing extension which shields said switches from inadvertent spillage during placement of said reservoir container in said well.

10. Apparatus according to claim 1, wherein said control means includes a foot switch attached to said housing by an elongate lead, and there is further included a hand piece connected to said pump means for delivery of the dental treatment solution to a patient.

11. Apparatus according to claim 1, wherein said pump means is a diaphragm pump, which pump is driven by a motor having a centrically mounted crank thereon with the crank arm being connected to said diaphragm, and said logic circuit means interrupts the supply of current to said motor in order to disable the supply of dental treatment solution.

12. Apparatus according to claim 1, wherein said pump means is a diaphragm pump which is driven by an electrically energized solenoid member in circuit with said control means.

13. Apparatus according to claim 12, wherein there is further provided means for adjusting the effective stroke of said solenoid, said means comprising stop means carried by said solenoid, and cam means disposed between the solenoid armature and said stop means having thereon portions of varying thickness such that upon operation of said cam means the stroke of said solenoid armature can be adjusted.

14. Apparatus according to claim 13, wherein said cam means is associated with a button disposed exteriorly of said housing, with spring means biasing said cam means and said buttom to a first position with depression of said button to a second position bringing a reduced thickness portion into alignment with said solenoid armature thereby effectively increasing the stroke of said solenoid armature and said diaphragm pump associated therewith.

15. Apparatus according to claim 1 wherein said pump means includes a pump housing, diaphragm means disposed within said housing, said housing including a first section and a second section, means clamping said sections together and said sections including means for sealingly clamping the periphery of said diaphragm, means on said housing section cooperating with said diaphragm to define a pumping chamber, and means for attaching said diaphragm to a source of reciprocal movement.

16. A diaphragm pumping assembly according to claim 15, wherein there is provided an opening in a first one of said housing members for attaching the diaphragm to a source of reciprocal movement, a second one of said housing sections including inlet port means and outlet port means in communication with the pumping chamber, and check valve means carried in operative association with said inlet and outlet port means.

17. A diaphragm pump assembly according to claim 16, wherein said inlet and outlet port means include valve chambers disposed immediately adjacent the pumping chamber defined by said diaphragm and said housing sections, an insert member disposed in said valve chamber, and a valve member carried by said insert member and preassembled thereto.

18. A diaphragm pump assembly according to claim 17, wherein said valving member is a ball member and said insert member includes a ball seat for sealing against flow in a preselected direction through said valve chamber.

19. A diaphragm pump assembly according to claim 15, wherein said diaphragm means comprises a first inner layer of material such as Teflon or the like which is nontoxic and will not react with the dental treatment solution, a second, outer elastomeric layer bonded to said first layer, a fastener member including a threaded shank portion extending from said second elastomeric layer and having an enlarged head portion disposed between said inner and outer layers, with said first inner layer overlying said head portion.

20. A diaphragm pump assembly according to claim 15, further including means for effecting reciprocal movement of said diaphragm, said means comprising a motor having an output shaft, an eccentric crank on said output shaft, a crank collar surrounding said eccentric shank and a crank arm operatively coupled to said diaphragm such that rotation of said output shaft will produce reciprocal movement of said crank arm and correspondingly reciprocal movement of said diaphragm.

21. A diaphragm pump assembly according to claim 20, further including means for adjusting the stroke of said crank arm and correspondingly the stroke of said diaphragm.

22. A diaphragm pump assembly according to claim 21, wherein said means for adjusting the stroke of the crank arm comprises a rotatably mounted adjustment ring disposed over the crank pin of said crank member and including an eccentrically disposed aperture receiving said crank pin, said crank collar member encircling said adjustement ring such that upon rotation of said adjustment ring, the degree of eccentric mounting of said collar and crank arm relative to said motor ouput shaft may be varied thereby varying the stroke of said crank arm.

23. Apparatus for delivery of a dental treatment solution or the like to a patient wherein said solution has a predetermined usable life cycle after initial formulation, said apparatus comprising: a reservoir container for said dental treatment solution; electrically operably pump means connectable with said reservoir container, with said pump means drawing solution out of said reservoir container for delivery to a hand piece for application to a patient and further including filter means disposed between said reservoir container and said pump means; conduit means leading from said pump and connectable to a hand piece, control means for said pump means including timer means actuated upon the operative connection of said reservoir container with said pump means, and logic circuit means for interrupting the power supply to said pump means after expiration of a prescribed period of time following operative connection of said reservoir container with said pump means, and further comprising an additional pump means connected to said conduit means downstream of said first mentioned pump means, said additional pump means being operable to purge said conduit means of expired dental treatment solution, when desired.

24. Apparatus according to claim 23, further including heater means disposed in said conduit means between said pump means and said point of delivery to a hand piece.

25. Apparatus according to claim 23, wherein said pump means is a diaphragm pump, and there is provided drive means for said diaphragm pump in the form of a motor having an eccentrically mounted crank with a crank arm connected to said diaphragm.

26. Apparatus according to claim 23, wherein said pump means is a diaphragm pump and there is provided an electrically energized solenoid, having the armature thereof connected to said diaphragm pump.

27. Apparatus according to claim 26, wherein there is further provided cam means for selectively controlling the stroke of said armature.

28. Apparatus according to claim 27, wherein said cam means is provided by a cam member disposed between said armature and an armature stop member, said cam means having at least two portions of varing thickness and being selectively operable to dispose said portions for controlling the stroke of said armature.

29. Apparatus for delivery of a dental treatment solution or the like, said apparatus comprising a housing including wall structure defining a well, a reservoir container for the dental treatment solution disposable in said well, said reservoir container including a lid pivotally mounted thereto, pivot means defining a pivot point for the lid which is disposed sufficiently below the upper level of said reservoir container such that when said container is positioned in said well, the wall structure of said well inhibits opening pivotal movement of said lid.

30. Apparatus according to claim 29, wherein said housing wall structure defining said well includes a bottom wall, and drain means is formed in said bottom wall to relieve any spillage of the dental treatment solution during positioning of the reservoir container therein.

31. Apparatus according to claim 29, wherein said reservoir container includes a bottom wall structure and valve means carried by said bottom wall structure, said housing including means for engaging and opening said valve means upon disposition of said reservoir container into said well.

32. Apparatus according to claim 29, wherein the pivot means for affixing said lid to said container includes a pair of pivot pins on opposite sides of said container, a pair of flanges on opposite sides of said lid corresponding to said pivot pins, each said flange including an elogate slot for receiving said pivot pin, which slot provides for lateral movement of the lid with respect to said container during opening pivotal movement thereof.

33. Apparatus according to claim 32, wherein said lid further includes a pair of detent means engageable with the upper rim of said reservoir container, such that said lid can be maintained in an intermediate open position.

34. Apparatus for delivery of a dental treatment solution or the like, said apparatus comprising a housing including wall structure which defines a well portion, a reservoir container for the dental treatment solution disposable in said well portion, said well portion including an elongate opening extending to the front of said housing, said reservoir container including a transparent extension portion received in said elongate well opening and viewable from the exterior of said housing to thereby provide a visual indication of the level of dental treatment solution in said reservoir container, and further including a relieved portion adjacent and beneath said elongate housing opening to provide a finger grip, whereby said reservoir may be gripped by said extension portion and removed.

35. Apparatus according to claim 34, wherein said reservoir container includes a bottom wall structure and valve means carried by said bottom wall structure, said housing including means for engaging an opening in said valve means upon disposition of said reservoir container into said well portion.

36. Apparatus according to claim 34, wherein said well portion includes a bottom wall, and drain means formed in said bottom wall to relieve any spillage which may occur during disposition of said reservoir container in said well.

37. Apparatus for delivery of a dental treatment solution or the like, said apparatus comprising, a housing having pumping means and control means for said pumping means, and including wall structure defining a well portion, a reservoir container for the dental treatment solution disposable in said well portion, said housing well portion including a bottom wall, and a series of drain holes formed in said bottom wall to alleviate any spillage during disposition of said reservoir container in said well portion, said reservoir container including a bottom well structure and valve means carried by said bottom wall structure, and further incuding at least three leg members extending from the bottom wall portion thereof and being of sufficient length to extend past said valve means, said leg members being receivable in the drain holes provided in the bottom of said well portion, said housing including conduit means leading to said pump means and means for engaging and opening said valve means upon disposition of said reservoir container into said well portion.

38. Apparatus according to claim 37, wherein the wall structure defining said well portion includes an elongate opening extending to the front of said housing, and said reservoir container further includes a transparent extension portion received in said elongate well opening and viewable from the exterior of said housing to provide a visual indication as to the level of dental treatment solution in said reservoir container.

39. A reservoir container for use with apparatus for delivery of a dental treatment solution or the like, said reservoir container adapted to be disposed within a well portion and operatively connected to pumping means of said apparatus, said reservoir container including a body portion having an upper open rim, a cover member, means pivotally connecting the cover member to the body portion, said means comprising a pair of pivot pins extending from the opposite sidewalls of said body portion and disposed below the level of the upper rim of said body portion, said cover including a pair of flange members disposed on opposite sides thereof, and each said flange member having elongate slot means formed therein for reception of said pivot pin on the body portion, and detent means on said cover for engaging the rim such that when said detent means are so engaged a first open position is defined for said cover member, the pivot pins engaged in an upper region of said elongate slots, and said cover being movable to a second, fully open position upon disengagement of said detent means from said rim and upon disposition of said pivot pins in a lower region of said slots.

40. A reservoir container according to claim 39, wherein said container includes a bottom wall portion and valve means carried by said bottom wall structure and extending from the side thereof opposite that in which said dental treatment solution is housed, leg means also extending from said bottom wall structure and extending past said valve means, so that the reservoir container may be disposed upon a support surface without said valve means engaging said support surface.

41. A reservoir container according to claim 39 wherein said container includes an elongate transparent extension extending from a forward portion of said reservoir container and extending for the full height of said container, said transparent extension being adapted to be received within an opening in a well structure designed for reception of said reservoir container and for providing a visual indication as to the level of dental treatment solution in said reservoir container.

42. Apparatus for delivery of a dental treatment solution or the like, said apparatus comprising: a housing defined by upper and lower sections, said upper section including means providing a reservoir for a quantity of dental solution, pump means and control means for said pump means disposed interiorly of said housing, said control means including means for sensing the positioning of the reservoir container in said well, and logic circuit means for disabling the supply of dental treatment solution upon the elapse of a prescribed period of time after the reservoir is positioned in said well, and heater means for heating the dental solution preparatory to delivery to the patient, a chassis member provided as a separate component with respect to said upper and lower housing sections, said chassis member having said pump means, said heater means and said control means for the pump means mounted theron, and said chassis being mountable to one of said housing upper and lower sections.

43. Apparatus according to claim 42, wherein said upper housing section includes wall structure defining a well portion, and there is provided a separate reservoir container disposable in said well portion.

44. Apparatus according to claim 42, wherein said control means mounted to said chassis includes a lead for attachment to a power source, and a foot switch attached to said control means by an elongate lead.

45. Apparatus according to claim 42, wherein there is further included a hand piece for delivery of the dental treatment solution to a patient, said hand piece being attached to said pump means by an elongate conduit, and said upper housing section including hand piece holding means in the form of pair of U-shaped brackets mounted to a side portion of said upper housing section.

* * * * *